(12) United States Patent
Allison et al.

(10) Patent No.: US 7,057,081 B2
(45) Date of Patent: Jun. 6, 2006

(54) METHOD FOR TREATING ALKANES

(75) Inventors: Joe D. Allison, Ponca City, OK (US);
Steven R. McDonald, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 341 days.

(21) Appl. No.: 10/436,684

(22) Filed: May 9, 2003

(65) Prior Publication Data

US 2004/0225165 A1 Nov. 11, 2004

(51) Int. Cl.
C07C 29/74 (2006.01)
(52) U.S. Cl. .................. 568/910.5; 568/300; 568/700; 568/840; 568/909; 568/910
(58) Field of Classification Search ............... 568/300, 568/700, 840, 909, 910, 910.5
See application file for complete search history.

(56) References Cited

U.S. PATENT DOCUMENTS

| | | | | |
|---|---|---|---|---|
| 3,758,615 | A | 9/1973 | Izumi et al. ................. | 260/641 |
| 3,955,939 | A | 5/1976 | Sommer et al. ................ | 44/53 |
| 4,484,013 | A * | 11/1984 | Schmidt ..................... | 568/899 |
| 5,550,309 | A * | 8/1996 | Maunders et al. ........... | 585/654 |
| 6,409,940 | B1 | 6/2002 | Gaffney et al. ............. | 253/373 |
| 2002/0133050 | A1 | 9/2002 | Chuang et al. ............. | 568/895 |

FOREIGN PATENT DOCUMENTS

BE 683923 9/1966

OTHER PUBLICATIONS

"*Petroleum Chemicals at Wilton*," Petroleum, pp. 19-21, Jan. 1953.
"*Isopropanol*," Hydrocarbon Processing, vol. 46, No. 11, p. 195, Nov. 1967.
"*VEBA Process Leads in Isopropanol Expansion*," European Chemical News, p. 32 (cont'd on 34), Jul. 24, 1970.
"*Use Cation Catalyst for IPA*," W. Neier et al., Hydrocarbon Processing, pp. 113-116, Nov. 1972.
"*Isopropanol*," Deutsche Texaco AG, Hydrocarbon Processing, p. 141, 1973.
"*Propylene and its Industrial Derivatives*," J. C. Fielding, E. C. Hancock, Editor, p. 8-9, John Wiley & Sons, Inc., New York, 1973.
"*Isopropyl Alcohol by Direct Hydration*," W. Neier and J. Woellner, Chemtech, pp. 95-99, Feb. 1973.
"*Isopropanol durch Direkthydratation von Propylen mit Wasser*," W. Neier and J. Woellner, Erdol und Kohle, pp. 19-24, Jan. 1975.
"*Hydration with Water*," Y. Onoue, et al., Chemtech, pp. 432-435, Jul. 1978.
"*Isopropanol*," Deutsche Texaco AG, Hydrocarbon Processing, p. 181, Nov. 1979.
"*Isopropyl Alcohol*," Philip J. Chenier, Survey of Industrial Chemistry, $2^{nd}$ Edition, pp. 196-200, 1992.
"*Proply Alcohols*," J. E. Logsdon, et al., Kirk-Othmer Encyclopedia of Chemical Technology, Fourth Edition, vol. 20, 216-241, 1996.
"*Alcohols*," K. Weissermel and H. J. Arpe, Industrial Organic Chemistry, $3^{rd}$ Edition, pp. 196-199, 1997.
"*Alcohols*," K. Weissermel, Industrial Organic Chemistry, $3^{rd}$ Edition, pp. 192-196, 1999.
"*Vinyl-Halogen and Vinyl-Oxygen Compounds*," K. Weissermel and H. J. Arpe, Industrial Organic Chemistry, $3^{rd}$ Edition, pp. 223-231, 1999.

* cited by examiner

*Primary Examiner*—Johann Richter
*Assistant Examiner*—Chukwuma Nwaonicha
(74) *Attorney, Agent, or Firm*—Conley Rose P.C.

(57) ABSTRACT

Methods are disclosed for converting propane and higher alkanes to their corresponding alcohols through a multi-step process with olefin as an intermediate. Methods are also disclosed for facilitating the transportation, purification or other treatment of propylene and higher olefins using a chemical conversion to the corresponding alcohol and reconversion to olefin. Methods are also disclosed for converting propane and higher alkanes to olefins using the corresponding alcohol as a temporary intermediate to minimize purification, transportation and/or other treatment costs.

10 Claims, 3 Drawing Sheets

METHOD FOR TREATING ALKANES

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Technical Field of the Invention

The present invention is directed towards downstream treatment and purification of olefins generated by dehydrogenation of alkanes. More particularly, the present invention is directed toward a process for generating alcohols from alkanes by dehydrogenating one or more alkanes to olefins followed by hydrating the olefins to alcohols.

2. Description of Related Art

There is currently a significant interest in various types of hydrocarbon processing reactions. One such class of reactions involves the chemical conversion of natural gas, a relatively low value reactant, to higher value products. Natural gas comprises several components, including alkanes. Alkanes are saturated hydrocarbons—i.e., compounds consisting of hydrogen (H) and carbon (C)—whose molecules contain carbon atoms linked together by single bonds. The principal alkane in natural gas is methane; however, significant quantities of longer-chain alkanes such as ethane ($CH_3CH_3$), propane ($CH_3CH_2CH_3$), and butane ($CH_3CH_2CH_2CH_3$) may also be present. Unlike longer-chain alkanes, these short-chain alkanes are gaseous under ambient conditions.

The interest in the chemical conversion of the methane and higher alkanes in natural gas stems from a variety of factors. First, vast reserves of natural gas have been found in remote areas where no local market exists. There is great incentive to exploit these natural gas formations because natural gas is predicted to outlast liquid oil reserves by a significant margin. Unfortunately, though, the transportation costs for gaseous alkanes are generally high, primarily because of the extremely low temperatures needed to liquefy these highly volatile gases for transport. Consequently, there is considerable interest in techniques for converting gaseous alkanes to higher value, more easily transported products at the remote site.

Several hydrocarbon processing techniques are currently being investigated for the chemical conversion of lower alkanes. One such technique involves the conversion of methane to higher chain-length alkanes that are liquid or solid at room temperature. This conversion of methane to higher hydrocarbons is typically carried out in two steps. In the first step, methane is partially oxidized to produce a mixture of carbon monoxide and hydrogen known as synthesis gas or syngas. In a second step, the syngas is converted to liquid and solid hydrocarbons using the Fischer-Tropsch process. This method allows the conversion of synthesis gas into liquid hydrocarbon fuels and solid hydrocarbon waxes. The high molecular weight waxes thus produced provide an ideal feedstock for hydrocracking, which ultimately yields high quality jet fuel and superior high cetane value diesel fuel blending components.

Another important class of hydrocarbon processing reactions are dehydrogenation reactions. In a dehydrogenation process, alkanes can be dehydrogenated to produce alkenes. Alkenes, also commonly called olefins, are unsaturated hydrocarbons whose molecules contain one or more pairs of carbon atoms linked together by a double bond. Generally, olefin molecules are represented by the chemical formula R'CH=CHR, where C is a carbon atom, H is a hydrogen atom, and R and R' are each an atom or a pendant molecular group of varying composition. One example of a dehydrogenation reaction is the conversion of ethane to ethylene [1]:

$$C_2H_6 + \text{Heat} \rightarrow C_2H_4 + H_2 \qquad [1].$$

The non-oxidative dehydrogenation of ethane to ethylene is endothermic, meaning that heat energy must be supplied to drive the reaction. Similarly, propane and higher alkanes may be dehydrogenated to yield olefins.

Alkenes such as ethylene and propylene are typically higher value chemicals than their corresponding alkanes. This is true, in part, because alkenes are important feedstocks for producing various commercially useful materials such as detergents, high-octane gasolines, pharmaceutical products, plastics, synthetic rubbers and viscosity additives. Ethylene, a raw material in the production of polyethylene, is the one of the most abundantly produced chemicals in the United States. Propylene is also a raw material in a number of different processes and is utilized on a large scale. Consequently, cost-effective methods for producing these olefins are of great commercial interest.

Traditionally, the dehydrogenation of hydrocarbons has been carried out using fluid catalytic cracking (FCC), a non-oxidative dehydrogenation process, or steam cracking. Heavy alkenes, those containing five or more carbon atoms, are typically produced by FCC; in contrast, light olefins, those containing two to four carbon atoms, are typically produced by steam cracking. FCC and steam cracking have several drawbacks. First, both processes are highly endothermic, thus requiring input of energy. In addition, some of the alkane reactant is lost as carbon deposits known as coke. These carbon deposits not only decrease yields but also deactivate the catalysts used in the FCC process. The costs associated with heating, yield loss and catalyst regeneration render these processes expensive even without regard to catalyst cost.

Recently, there has been increased interest in oxidative dehydrogenation (ODH) as an alternative to FCC and steam cracking. In ODH, alkanes are dehydrogenated in the presence of an oxidant such as oxygen, typically in a short contact time reactor containing an ODH catalyst. ODH can be used, for example, to convert ethane and oxygen to ethylene and water [2]:

$$C_2H_6 + 1/2 O_2 \rightarrow C_2H_4 + H_2O + \text{Heat} \qquad [2].$$

Thus, ODH provides an alternative chemical route for generating ethylene from ethane. Similarly, ODH may be used to generate higher olefins (e.g., propylene and butylenes) from corresponding alkanes. Unlike non-oxidative dehydrogenation, however, ODH is exothermic, meaning that it produces rather than requires heat energy.

Although ODH involves the use of a catalyst, which is referred to herein as an ODH catalyst, and is therefore literally a catalytic dehydrogenation, ODH is distinct from what is normally called "catalytic dehydrogenation" in that the former involves the use of an oxidant and the latter does not. ODH is attractive because, among other reasons, the capital costs for olefin production via ODH are significantly less than with the traditional processes. ODH, unlike traditional FCC and steam cracking, can be employed using simple fixed bed reactor designs and high volume throughput.

More important, however, is the fact that ODH is exothermic. The net ODH reaction can be viewed as two separate processes: an endothermic dehydrogenation of an alkane coupled with a strongly exothermic combustion of hydrogen, as depicted in [3]:

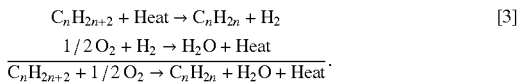

$$\frac{\begin{array}{l}C_nH_{2n+2} + \text{Heat} \rightarrow C_nH_{2n} + H_2 \\ 1/2\,O_2 + H_2 \rightarrow H_2O + \text{Heat}\end{array}}{C_nH_{2n+2} + 1/2\,O_2 \rightarrow C_nH_{2n} + H_2O + \text{Heat}}. \quad [3]$$

Energy savings over traditional, endothermic processes can be especially significant if the heat produced in the ODH process is recaptured and recycled. Unfortunately, although ODH offers the possibility of cost-effective olefin production, the high cost for short-chain alkane and olefin transportation has limited interest in the exploitation of remote site natural gas.

BRIEF SUMMARY OF PREFERRED EMBODIMENTS

Some of the preferred embodiments of the present invention relate to methods for sequentially converting alkanes to olefins and then to the corresponding alcohol. Preferably, the alkane is converted to an olefin using catalytic oxidative dehydrogenation and the olefin is converted to the corresponding alcohol by direct catalytic hydration. According to some preferred embodiments, the alcohol is purified and/or transported. Following purification and/or transportation, the alcohol may be dehydrated to yield an olefin. Some of the preferred embodiments of the present invention relate to products prepared according to the methods described.

BRIEF DESCRIPTION OF THE DRAWINGS

For a more detailed description of the present invention, reference will now be made to the accompanying drawings, wherein.

DETAILED DESCRIPTION OF PREFERRED EMBODIMENTS

The preferred embodiments of the present invention comprise various combinations of dehydrogenation hydration, and dehydration reactions. Some preferred embodiments derive from the conception of a novel method of producing alcohols from alkanes such as propane using a combination of dehydrogenation and hydration reactions. Other preferred embodiments of the present invention derive from the conception of a novel technique for reducing olefin transportation and/or purification costs by hydrating one or more olefins to their respective alcohols, purifying and/or transporting the alcohol, and then dehydrating the alcohol to olefin.

The methods disclosed herein may be applied to a variety of alkane/olefin/alcohol systems. Therefore, without limiting the scope of the invention, the preferred embodiments of the present invention comprise a propane/propylene/isopropanol system or a butane/butene/2-butanol system. Isopropanol (also called isopropyl alcohol) and 2-butanol are highly versatile chemicals and are useful in a variety of capacities including the manufacturing of agricultural chemicals, pharmaceuticals, process catalysts and solvents. The intrinsic cost of each of these chemicals is fundamentally limited by the expense of the starting materials.

The synthesis of isopropanol or 2-butanol from propane or butane, respectively, derived from natural gas from remote areas offers a variety of benefits over prior art methods of preparing isopropanol and 2-butanol. First, the propane and butane in natural gas (particularly natural gas located at remote reserves) has a relatively low intrinsic cost when compared to the costs for alternative raw materials. Thus, the propane and butane in such natural gas is an economically-attractive starting material for isopropanol and 2-butanol manufacture. Second, the transportation costs of isopropanol and 2-butanol are relatively low when compared to the transportation costs of propane, propylene, butane or butylene. Thus, isopropanol and 2-butanol are attractive products for remote site manufacturing. For both of these reasons, the production of isopropanol and 2-butanol from propane and butane in natural gas from remote areas presents an attractive alternative to prior art methods.

Conversion of Alkane to Alcohol

Figure 1:
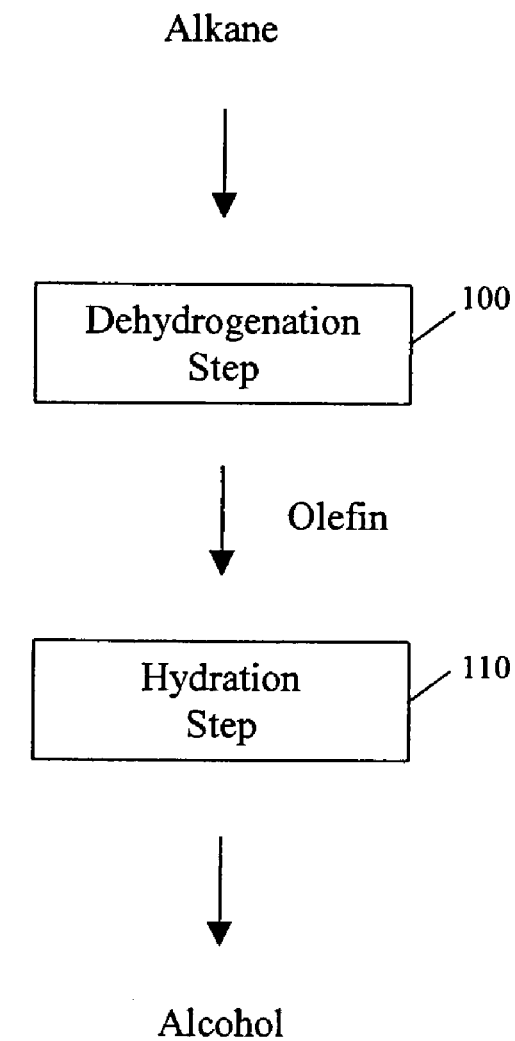
FIG. 1 depicts a simplified flow diagram for a multi-step process comprising a dehydrogenation/hydration reaction.

The preferred embodiments of the present invention relate to processes for the conversion of one or more alkanes to corresponding alcohols through a multi-step process comprising a combination of dehydrogenation and hydration reactions, depicted as a simplified flow diagram in FIG. 1. According to some of the preferred embodiments of the present invention, the process comprises a dehydrogenation step 100 in which the one or more alkanes are converted to their corresponding olefins. The dehydrogenation process can be any type of process capable of yielding olefins from alkanes. Preferably, the dehydrogenation process is one of those disclosed below. More preferably, the dehydrogenation process is a catalytic oxidative dehydrogenation process performed in a short contact time reactor.

The process also comprises a hydration step 110 in which the one or more olefins are converted to their corresponding alcohols. The hydration process can be any type of hydration process capable of yielding alcohols from olefins. Preferably, the hydration process is an embodiment disclosed below. More preferably, the hydration process is a direct catalytic hydration. The preferred dehydrogenation and hydration techniques are described in further detail below.

Figure 2:
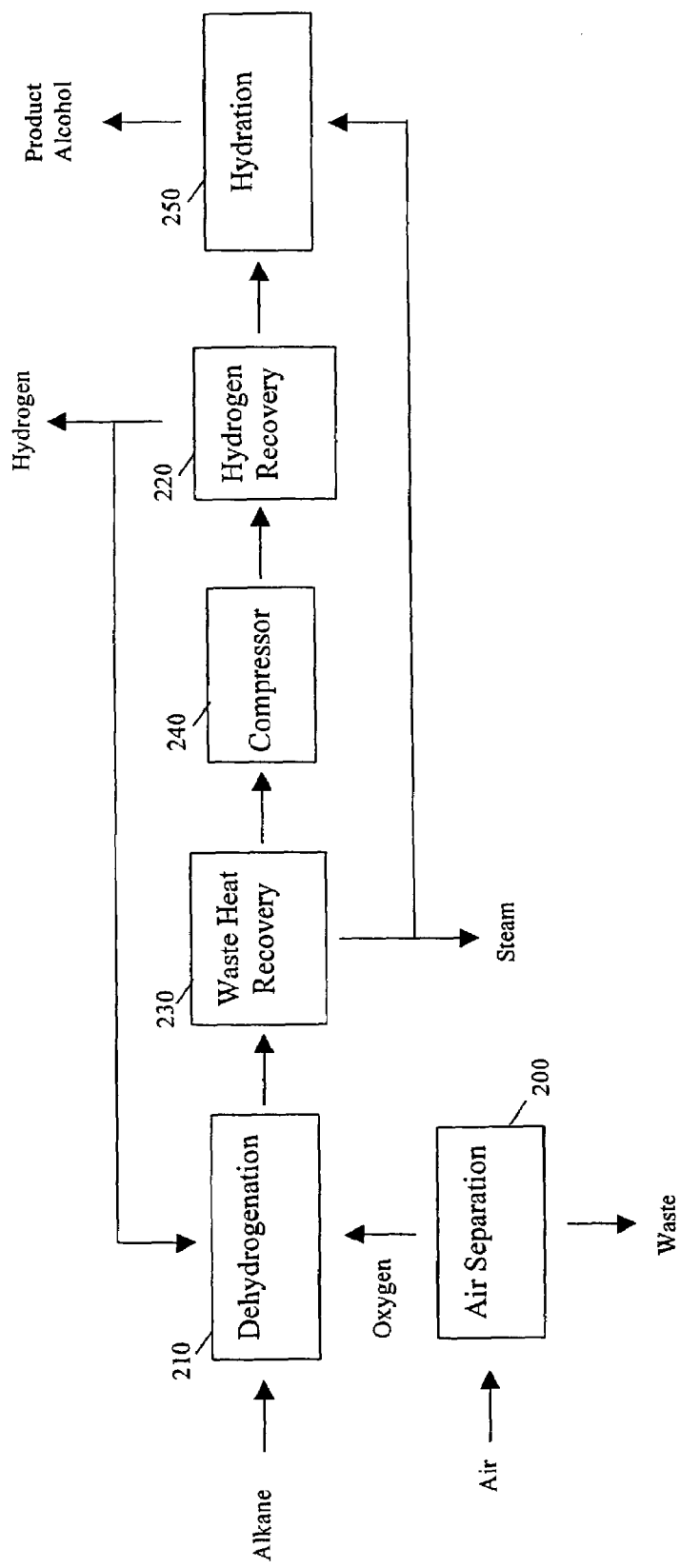
FIG. 2 depicts a block diagram schematic for a multi-step process comprising a dehydrogenation/hydration reaction.

FIG. 2 depicts a block diagram schematic for a preferred embodiment of the present invention. One or more alkanes from a natural gas stream and oxygen from an air separation unit (ASU) 200 are mixed and enter a dehydrogenation reactor 210 maintained under reaction promoting conditions. The alkane/oxygen feedstock can be supplemented by a hydrogen stream from hydrogen recovery unit 220, which is downstream of dehydrogenation reactor 210. The olefin product stream from dehydrogenation reactor 210 then passes through waste heat recovery unit 230 and compressor 240, which recover waste heat and pressurize the olefin product stream, respectively. The resulting cooled, pressurized olefin product stream passes through hydrogen recovery unit 220, which separates hydrogen present in the olefin product stream. Following hydrogen removal, the olefin product stream is converted to a corresponding alcohol stream in hydration reactor 250. As will be immediately evident to those of skill in the art, additional process steps—e.g., purification steps—are within the spirit and scope of the invention.

Preferred Methods for the Dehydrogenation of Alkanes

Any acceptable process for converting alkanes to olefins may be used in the present invention. Exemplary methods for preparing olefins from alkanes include, but are not limited to, fluidized catalytic cracking, steam pyrolysis and catalytic ODH. Therefore, without limiting the scope of the invention, the preferred embodiments of the present invention employ a catalytic ODH process as depicted in reaction [2] above.

As used herein, the term "ODH catalyst" refers to the overall catalyst including, but not limited to, any base metal, an optional promoter metal and refractory support. A variety of catalyst compositions are suitable as ODH catalysts. Without limiting the scope of the invention, the preferred embodiments employ a catalyst comprising a base metal and an optional promoter metal on a refractory support. Many promoter metals increase catalyst activity in ODH processes and are within the scope of the present invention. As an example, and without limiting the scope of the invention, promoter metals in ODH catalysts include Group VIII metals—i.e., platinum, rhodium, ruthenium, iridium, nickel, palladium, iron, cobalt and osmium. Platinum is a preferred promoter metal. However, as is evident to those of skill in the art, other promoter metals can also be used. Furthermore, a combination of promoter metals is also within the scope of the invention. Consequently, references herein to the promoter metal are not intended to limit the invention to one promoter metal.

As used herein, the term "promoter metal loading" refers to the percent by weight promoter metal in the ODH catalyst, measured as the weight of reduced promoter metal relative to the overall weight of the ODH catalyst. Preferably, the promoter metal loading is less than about 0.1 weight percent.

Some of the preferred embodiments of the present invention employ one or more base metals in addition to the promoter metal. A variety of base metals exhibit catalytic activity in ODH processes and are within the scope of the present invention. As an example, and without limiting the scope of the invention, base metals useful in the preferred embodiments of the present invention include Group IB-IIB metals, Group IVB-VIIB metals, Group IIA-VA metals, lanthanide metals, scandium, yttrium, actinium, iron, cobalt, nickel, their oxides and combinations thereof. More preferably, the base metal is selected from the group consisting of manganese, chromium, tin, copper, gold, their corresponding oxides and combinations thereof. A combination of base metals is within the scope of the invention. Consequently, references herein to the base metal are not intended to limit the invention to one base metal.

As used herein, the term "base metal loading" refers to the percent by weight base metal in the ODH catalyst, measured as the weight of reduced base metal relative to the overall weight of the ODH catalyst. When present, the base metal is preferably present at a base metal loading of between about 0.5 and about 20 weight percent, more preferably between about 1 and about 12 weight percent, and still more preferably between about 2 and about 6 weight percent.

Preferably, the base metal and the promoter metal, if present, are deposited on refractory supports configured as wire gauzes, porous monoliths, or particles. The term "monolith" refers to any singular piece of material of continuous manufacture such as solid pieces of metal or metal oxide or foam materials or honeycomb structures. Two or more such catalyst monoliths may be stacked in the catalyst zone of the reactor if desired. For example, the catalyst can be structured as, or supported on, a refractory oxide "honeycomb" straight channel extrudate or monolith, made of cordierite or mullite, or other configuration having longitudinal channels or passageways permitting high space velocities with a minimal pressure drop. Such configurations are known in the art and described, for example, in *Structured Catalysts and Reactors*, A. Cybulski and J. A. Moulijn (Eds.), Marcel Dekker, Inc., 1998, p. 599–615 (Ch. 21, X. Xu and J. A. Moulijn, "Transformation of a Structured Carrier into Structured Catalyst"), which is hereby incorporated herein by reference.

Some preferred monolithic supports include partially stabilized zirconia (PSZ) foam (stabilized with Mg, Ca or Y), or foams of α-alumina, cordierite, titania, mullite, Zr-stabilized α-alumina, or mixtures thereof. A preferred laboratory-scale ceramic monolith support is a porous alumina foam with approximately 6,400 channels per square inch (80 pores per linear inch). Preferred foams for use in the preparation of the catalyst include those having from 30 to 150 pores per inch (12 to 60 pores per centimeter). The monolith can be cylindrical overall, with a diameter corresponding to the inside diameter of the reactor tube.

Alternatively, other refractory foam and non-foam monoliths may serve as satisfactory supports. The promoter metal precursor and any base metal precursor, with or without a ceramic oxide support forming component, may be extruded to prepare a three-dimensional form or structure such as a honeycomb, foam or other suitable tortuous-path structure.

More preferred catalyst geometries employ distinct or discrete particles. The terms "distinct" or "discrete" particles, as used herein, refer to supports in the form of divided materials such as granules, beads, pills, pellets, cylinders, trilobes, extrudates, spheres, other rounded shapes or another manufactured configuration. Alternatively, the divided material may be in the form of irregularly shaped particles. Preferably at least a majority—i.e., greater than about 50 percent—of the particles or distinct structures have a maximum characteristic length (i.e., longest dimension) of less than six millimeters, preferably less than three millimeters. Preferably, these particulate-supported catalysts are prepared by impregnating or washcoating the promoter metal and base metal, if present, onto the refractory particulate support.

Numerous refractory materials may be used as supports in the present invention. Without limiting the scope of the invention, suitable refractory support materials include silicon carbide, boron carbide, tungsten carbide, silicon nitride, boron nitride, tungsten nitride, zirconia, magnesium stabilized zirconia, zirconia stabilized alumina, yttrium stabilized zirconia, calcium stabilized zirconia, alumina, cordierite, titania, silica, magnesia, niobia, vanadia, nitrides, silicon nitride, carbides, silicon carbide, cordierite, cordierite-alpha alumina, zircon mullite, spodumene, alumina-silica magnesia, zircon silicate, sillimanite, magnesium silicates, zircin, petalite, carbon black, calcium oxide, barium sulfate, silica-alumina, alumina-zirconia, alumina-chromia, alumina-ceria, and combinations thereof. Preferably, the refractory support comprises alumina, zirconia or combinations thereof. Alumina is preferably in the form of alpha-alumina (α-alumina); however, the other forms of alumina have also demonstrated satisfactory performance.

The base metal and promoter metal, when present, may be deposited in or on the refractory support by any method known in the art. Without limiting the scope of the invention, acceptable methods include incipient wetness impregnation, chemical vapor deposition, co-precipitation, and the like. Preferably, the base and promoter metals are deposited by the incipient wetness technique.

The preferred embodiments of the processes of the present invention employ an alkane feedstock comprising one or more alkanes and an oxidant feedstock that are mixed to yield a reactant mixture, which is sometimes referred to herein as the reactant gas mixture. Preferably, the alkane feedstock comprises ethane and/or propane and/or butane. The oxidant feedstock comprises an oxidant capable of oxidizing at least a portion of the alkane feedstock. Appropriate oxidants may include, but are not limited to, $I_2$, $O_2$, $N_2O$, $CO_2$ and $SO_2$. Use of the oxidant shifts the equilibrium of the dehydrogenation reaction toward complete conversion through the formation of compounds containing the abstracted hydrogen (e.g., $H_2O$ and HI). Preferably, the oxidant comprises a molecular oxygen-containing gas. Without limiting the scope of the invention, representative examples of acceptable molecular oxygen-containing gas feedstocks include pure oxygen gas, air and $O_2$-enriched air.

As depicted in equations [4], [5] and [6], the complete combustion of ethane, propane and butane require a stoichiometrically predictable quantity of oxygen:

$$C_2H_6 + 7/2\ O_2 \rightarrow 2\ CO_2 + 3\ H_2O \qquad [4]$$

$$C_3H_8 + 5\ O_2 \rightarrow 3\ CO_2 + 4\ H_2O \qquad [5].$$

$$C_4H_{10} + 13/2\ O_2 \rightarrow 4\ CO_2 + 5\ H_2O \qquad [6]$$

According to equations 4, 5 and 6, atomic oxygen-to-carbon ratios of 3.5:1, 3.3:1 and 3.25:1 represent the stoichiometric ratio for complete combustion of ethane, propane, and butane, respectively. Preferably, the composition of the reactant gas mixture is such that the atomic oxygen-to-carbon ratio is between about 0.05:1 and about 5:1. In some embodiments, the reactant mixture may also comprise steam. Steam may be used to activate the catalyst, remove coke from the catalyst, or serve as a diluent for temperature control. The ratio of steam to carbon by weight, when steam is added, may preferably range from about 0 to about 1.

Preferably, a short contact time reactor (SCTR) is used. Use of a SCTR for the commercial scale conversion of alkanes to olefins allows reduced capital investment and increases olefin production significantly. The preferred embodiments of the present invention employ a very fast contact (i.e., millisecond range)/fast quench (i.e., less than one second) reactor assembly such as those described in the literature. For example, co-owned U.S. Pat. No. 6,409,940 describes the use of a millisecond contact time reactor for use in the production of synthesis gas by catalytic partial oxidation of methane. The use of a similar reactor for ODH is described in a commonly-assigned currently-pending application entitled "Oxidative Dehydrogenation of Hydrocarbons Using Catalysts with Trace Catalytic Metal Loading," application Ser. No. 10/266,404. The disclosures of these references are hereby incorporated herein by reference.

The ODH catalyst may be configured in the reactor in any arrangement including fixed bed, fluidized beds or ebulliating bed (sometimes referred to as ebullating bed) arrangements. A fixed bed arrangement employs a stationary catalyst and a well-defined reaction volume whereas a fluidized bed utilizes mobile catalyst particles. Conventional fluidized beds include bubbling beds, turbulent fluidized beds, fast fluidized beds, concurrent pneumatic transport beds, and the like. A fluidized bed reactor system has the advantage of allowing continuous removal of catalyst from the reaction zone, with the withdrawn catalyst being replaced by fresh or regenerated catalyst. A disadvantage of fluidized beds is the necessity of downstream separation equipment to recover entrained catalyst particles. Preferably, the catalyst is retained in a fixed bed reaction regime in which the catalyst is retained within a well-defined reaction zone. Fixed bed reaction techniques are well known and have been described in the literature. Irrespective of catalyst arrangement, the reactant mixture is contacted with the catalyst in a reaction zone while maintaining reaction promoting conditions.

The reactant gas mixture is heated prior to or as it passes over the catalyst such that the reaction initiates. In accordance with one preferred embodiment of the present invention, a method for the production of olefin includes contacting a preheated reactant gas mixture with a catalyst containing a Group VIII metal and a refractory support sufficient to initiate oxidative dehydrogenation, maintaining a contact time of the reactant gas mixture with the catalyst for less than about 30 milliseconds, and maintaining oxidative dehydrogenation promoting conditions. Preferably, the ODH catalyst composition and the reactant gas mixture composition are such that oxidative dehydrogenation promoting conditions can be maintained with a preheat temperature of about 600° C. or less. More preferably, the ODH catalyst composition and the reactant mixture composition are such that oxidative dehydrogenation promoting conditions can be maintained with a preheat temperature of about 300° C. or less.

Reaction productivity, conversion and selectivity are affected by a variety of processing conditions including temperature, pressure, gas hourly space velocity (GHSV) and catalyst arrangement within the reactor. As used herein, the term "maintaining reaction promoting conditions" refers to controlling these reaction parameters, as well as reactant mixture composition and catalyst composition, in a manner in which the desired ODH process is favored.

The reactant gas mixture may be passed over the catalyst in any of a wide range of gas hourly space velocities. Gas hourly space velocity (GHSV) is defined as the volume of reactant gas per volume of catalyst per unit time. Although for ease in comparison with prior art systems space velocities at standard conditions have been used to describe the present invention, it is well recognized in the art that residence time is inversely related to space velocity and that high space velocities correspond to low residence times on the catalyst and vice versa. High throughput systems typically employ high GHSV and low residence times on the catalyst.

Preferably, GHSV for the present process, stated as normal liters of gas per liters of catalyst per hour, ranges from about 20,000 to about 200,000,000 $hr^{-1}$, more preferably from about 50,000 to about 50,000,000 $hr^{-1}$. The GHSV is preferably controlled so as to maintain a reactor residence time of no more than about 30 milliseconds for the reactant gas mixture. An effluent stream of product gases including olefin, unconverted alkane, $H_2O$ and possibly CO, $CO_2$, $H_2$ and other byproducts exits the reactor. In a preferred embodiment, the alkane conversion is at least about 30 percent and the total olefin selectivity (i.e., the selectivity measured as the sum of all olefin products) is at least about 30 percent. More preferably, the alkane conversion is at least about 40 percent and the total olefin selectivity is at least about 40 percent. Still more preferably, the alkane conversion is at least about 50 percent and the total olefin selectivity is at least about 50 percent.

Hydrocarbon processing techniques typically employ elevated temperatures to achieve reaction promoting conditions. According to some preferred embodiments of the present invention, the step of maintaining reaction promoting conditions includes preheating the reactant mixture to a temperature between about 30° C. and about 750° C., more preferably not more than about 600° C. The ODH process typically occurs at temperatures of from about 450° C. to about 2,000° C., more preferably from about 700° C. to about 1,200° C. As used herein, the terms "autothermal," "adiabatic" and "self-sustaining" mean that after initiation of the hydrocarbon processing reaction, additional or external heat need not be supplied to the catalyst in order for the production of reaction products to continue. Under autothermal or self-sustaining reaction conditions, exothermic reactions provide the heat for endothermic reactions, if any. Consequently, under autothermal process conditions, an external heat source is generally not required.

Hydrocarbon processing techniques frequently employ atmospheric or above atmospheric pressures to maintain reaction promoting conditions. Some embodiments of the present invention entail maintaining the reactant gas mixture at atmospheric or near-atmospheric pressures of approximately 1 atmosphere while contacting the catalyst. Advantageously, certain preferred embodiments of the process are operated at above atmospheric pressure to maintain reaction promoting conditions. Some preferred embodiments of the present invention employ pressures up to about 32,000 kPa (about 320 atmospheres), more preferably between about 200 and about 10,000 kPa (between about 2 and about 100 atmospheres).

Preferred Methods for the Hydration of Olefins

A wide range of olefins may be converted to alcohols by hydration. Therefore, without limiting the scope of the invention, the preferred embodiments are directed to ethanol, isopropanol, and 2-butanol generation from ethane, propane and butane, respectively. Any acceptable process may be used in the present invention. Exemplary methods have been previously described in, for example, K. Weissermel and H. J. Arpe, *Industrial Organic Chemistry* (3d Ed., 1999) pp. 191–196 and J. E. Logsdon, Ethanol, Kirk-Othmer Encyclopedia of Chemical Technology, Fourth Edition, Volume 9, 812–860, 1994, which is hereby incorporated by reference. Therefore, without limiting the scope of the invention, the preferred embodiments of the present invention employ two well known routes for hydrating olefins to alcohols: indirect and direct hydration.

First, ethanol may be formed from ethylene in a two-step indirect process employing concentrated $H_2SO_4$ and water. According to this process, ethylene is initially reacted with concentrated $H_2SO_4$ to yield a sulfuric acid ester as depicted in reaction [7]:

$$C_2H_4 + H_2SO_4 \rightarrow C_2H_5OSO_3H \qquad [7].$$

Typical process temperatures are between about 55 and about 80° C. and typical process pressures are between about 10 and about 35 bar.

The sulfuric acid ester is then hydrolyzed with water according to reaction [8], yielding ethanol and regenerated $H_2SO_4$:

$$C_2H_5OSO_3H + H_2O \rightarrow C_2H_5OH + H_2SO_4 \qquad [8].$$

Typical process temperatures for the hydration step are between about 70 and about 100° C. Thus, the net reaction is to hydrate ethylene to ethanol as depicted in reaction [9]:

$$C_2H_4 + H_2O \rightarrow C_2H_5OH \qquad [9].$$

More preferably, the ethanol is prepared from ethylene by direct catalytic hydration. This reversible reaction is typically carried out in the gas phase over acidic catalysts as depicted in reaction [10]:

$$C_2H_4 + H_2O \underset{}{\overset{[H^+]}{\rightleftharpoons}} C_2H_5OH. \qquad [10]$$

Although a number of acid catalysts may be used, $H_3PO_4$/$SiO_2$ catalysts are particularly useful in this process. Typical process temperatures are between about 200 and about 400° C. and typical process pressures are between about 40 and about 100 bar. Because single-pass ethanol yields are typically equilibrium limited in the direct catalytic hydration process, unconverted ethylene is preferably recycled to increase yield.

Similarly, any acceptable process for converting propylene to isopropanol may be used in the present invention. Such processes are known to those of skill in the art. Without limiting the scope of the invention, exemplary methods have been previously described in, for example, K. Weissermel and H. J. Arpe, *Industrial Organic Chemistry* (3d Ed., 1999) pp. 196–199 and J. E. Logsdon and R. A. Loke, Propyl Alcohols, Kirk-Othmer Encyclopedia of Chemical Technology, Fourth Edition, Volume 20, 216–240, 1996, which are hereby incorporated by reference. Therefore, without limiting the scope of the invention, the preferred embodiments of the present invention employ two well known routes for hydrating propylene to yield isopropanol.

First, isopropanol may be formed from propylene in a two-step indirect process employing concentrated $H_2SO_4$ and water. According to this process, propylene is initially reacted with concentrated $H_2SO_4$ to yield a sulfuric acid ester as depicted in reaction [11]:

$$C_3H_8 + H_2SO_4 \rightarrow (CH_3)_2CHOSO_3H \qquad [11].$$

Typical process temperatures are between about 20 and about 80° C. and typical process pressures are between about 8 and about 28 bar.

The sulfuric acid ester is then hydrolyzed with water according to reaction [12], yielding isopropanol and regenerated $H_2SO_4$:

$$(CH_3)_2CHOSO_3H + H_2O \rightarrow (CH_3)_2CHOH + H_2SO_4 \qquad [12].$$

Typical process temperatures for the hydration step are between about 70 and about 100° C. Thus, the net reaction is to hydrate propylene to isopropanol as depicted in reaction [13]:

$$C_3H_6 + H_2O \rightarrow (CH_3)_2CHOH \qquad [13].$$

The indirect catalytic hydration may be conducted in at least two different operational modes. In the two-step strong acid process, separate reactors are used. The formation of the sulfuric acid ester is conducted using a high sulfuric acid concentration (typically greater than about 80 weight percent), low pressures (typically between about 10 and about 12 bar), and low temperatures (typically between about 20 and about 30° C.). The weak acid process, in contrast, is conducted in a single stage using a lower sulfuric acid concentration (typically between about 60 and about 80 weight percent), higher pressures (typically about 25 bar), and higher temperatures (typically between about 60 and about 65° C.).

The sulfate ester hydrosylate is then stripped to yield a mixture of isopropyl alcohol, isopropyl ether, and water overhead, and dilute sulfuric acid bottoms. Next, the overhead is neutralized (by, e.g., sodium hydroxide) and then refined in a two-column distillation system. The first isopropyl ether column redirects the ether to the reactor to produce additional isopropyl alcohol. The second column separates the wet isopropyl alcohol product, which may be utilized as is or dehydrated by, e.g., azeotropic distillation. The dilute sulfuric acid bottoms are passed to an acid reconcentration unit for upgrading to the proper concentration and recycling to the reactor. The purification of the resulting isopropanol and separation and recycling of other products (including the sulfuric acid catalyst) is within the knowledge of one of skill in the art.

Alternatively, the isopropanol may be prepared from propylene by direct catalytic hydration. This reversible reaction is typically carried out in the gas phase over acidic catalysts as depicted in reaction [14]:

$$C_3H_6 + H_2O \xrightleftharpoons{[H^+]} (CH_3)_2CHOH. \quad [14]$$

Without limiting the scope of the invention, at least three processes have proved commercially viable for the direct hydration of propylene. First, propylene may be hydrated to isopropanol in a high temperature and pressure gas-phase process using a silica-supported tungsten oxide catalyst with a zinc oxide promoter or a silica-supported phosphoric acid catalyst. The silica-supported tungsten oxide catalyst process has been described in J. C. Fielding, in E. C. Hancock, ed., *Propylene and Its Industrial Derivatives*, John Wiley & Sons, Inc, New York, 1973; K. Weissermel and H. J. Arpe, *Industrial Organic Chemistry*, Springer-Verlag, Weinheim, Austria, 1978; *Petroleum* (London), 16, 19 (1953), which are hereby incorporated by reference herein. The silica-supported phosphoric acid catalyst process has been described in Belgian Patent No. 683,923 (Dec. 16, 1966); *Hydrocarbon Processing*, 46(11), 195 (1967); U.S. Pat. No. 3,955,939 (May 11, 1976); and *European Chemical News*, 32 (Jul. 24, 1970), which are hereby incorporated by reference herein.

Second, propylene may be hydrated to isopropanol in a liquid phase trickle-bed process as described in W. Neier and J. Woellner, *Chemtech*, 95 (February 1973); Hydrocarbon Processing, 58(11), 181(1979); W. Neier and J. Woellner, *Erdoel Kohle*, 28(1), 19 (1975); W. Neier and J. Woellner, *Hydrocarbon Processing*, 5(11), 113 (1972); and *Hydrocarbon Processing*, 52(11) 141 (1973), which are hereby incorporated by reference herein. In this process, a mixture of liquid water and propylene gas in a molar ratio of approximately 12:1 to about 15:1 is introduced into the top of a fixed bed reactor and allowed to trickle down over a sulfonic acid ion-exchange resin. The reaction typically proceeds at temperatures between about 130 and about 160° C. and between about 80 and 100 atm.

Third, propylene may be hydrated to isopropanol in a liquid phase process employing a weakly acidic aqueous catalyst solution of a silico-tungstate, as described in Y. Onoue et al., *Chemtech*, 432 (July 1978) and U.S. Pat. No. 3,758,615, which are hereby incorporated by reference herein. A preheated mixture of propylene, water and catalyst solution are pressurized and fed into a reactor at a temperature of about 270° C. and a pressure of about 200 atm. After flashing the propylene, the resulting aqueous solution is separated by azeotropic distillation to yield catalyst (which is recycled) and an isopropanol product stream.

Although exemplary methods for hydrating ethylene and propylene have been shown, persons of skill in the art will recognize that the method is also applicable to other olefins (e.g., the hydration of butylene to 2-butanol).

Figure 3:
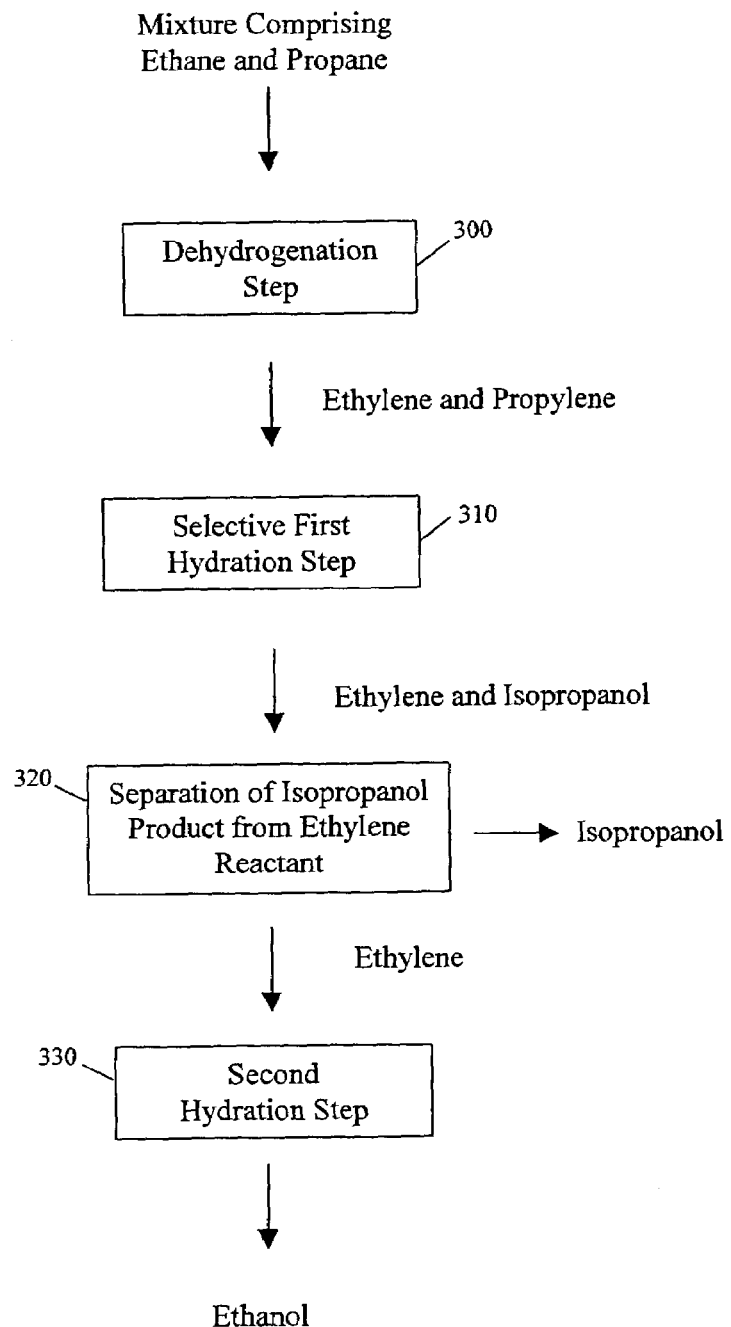
FIG. 3 depicts a simplified flow diagram for a multi-step process comprising a selective, sequential hydration reaction.

According to one preferred embodiment as depicted in FIG. 3, an olefin feedstock comprising both ethylene and propylene is hydrated under conditions that promote the selective hydration of one or more of, but not all of, the olefin components. Conditions promoting the selective hydration of the olefin components refers to reaction conditions that favor relatively the hydration of one or more olefin components while not favoring the hydration of one or more of the other olefin components. As used herein, the term "selective hydration" indicates that the molar hydration reaction rate with respect to the desired olefin reactant is at least ten times that of the not favored olefin. Under such selective hydration conditions, a mixture of different olefins can be sequentially hydrated and separated as distinct alcohol streams. For example, sequential hydration can be accomplished in an olefin stream comprising ethylene and propylene using indirect catalytic hydration because propylene can be hydrated under low temperatures conditions under which ethylene hydration is not favored.

First, as depicted in step 300 of FIG. 3, a mixture of alkanes comprising ethane and propane is dehydrogenated to yield a mixture of olefins. The mixture of olefins is then subjected in step 310 to low temperature conditions sufficient to hydrate isopropanol (as described previously) in a first hydration step. Second, in step 320, the newly-formed isopropanol product can then be separated from the ethylene reactant. Finally, in step 330, conditions are adjusted so as to favor ethanol formation from the ethylene (as described above) in a second hydration step. In this manner, two separate streams of ethanol and isopropanol can be generated from an ethylene/propylene mixture without the need for an additional separation step.

Preferred Methods for the Dehydration of Alcohols

Some of the preferred embodiments of the present invention employ the additional process of converting an alcohol to an olefin. Any acceptable process may be used in the present invention. Therefore, without limiting the scope of the invention, the preferred embodiments employ a dehydration process, as depicted in reactions [15], [16] and [17] for ethanol, isopropanol and 2-butanol, respectively:

$$C_2H_5OH \rightarrow C_2H_4 + H_2O \quad [15]$$

$$(CH_3)_2CHOH \rightarrow C_3H_6 + H_2O \quad [16]$$

$$CH_3CH_2CH(OH)CH_3 \rightarrow C_4H_8 + H_2O \quad [17].$$

The following commonly assigned application concurrently filed herewith is hereby incorporated herein by reference: "Method for Treating Ethane", application Ser. No. 10/436,685 filed concurrently herewith. Should the disclosure of any of the patents, patent applications, and publications that are incorporated herein conflict with the present specification to the extent that it might render a term unclear, the present specification shall take precedence.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

Accordingly, the scope of protection is not limited by the description set out above, but is only limited by the claims which follow, that scope including all equivalents of the subject matter of the claims. Each and every claim is incorporated into the specification as an embodiment of the present invention. Thus the claims are a further description and are an addition to the preferred embodiments of the present invention. Use of the term "optionally" with respect to any element of a claim is intended to mean that the subject element is required, or alternatively, is not required. Both alternatives are intended to be within the scope of the claim. The discussion of a reference in the Description of Related Art is not an admission that it is prior art to the present invention, especially any reference that may have a publication date after the priority date of this application. The disclosures of all patents, patent applications and publications cited herein are hereby incorporated herein by reference, to the extent that they provide exemplary, procedural or other details supplementary to those set forth herein.

What is claimed is:

1. A method for the production of alcohols having three or more carbon atoms from corresponding alkanes comprising:
    a) converting at least a portion of a reactant stream comprising propane and/or one or more longer-chain alkanes to an intermediate product stream comprising one or more corresponding olefins through a catalytic oxidative dehydrogenation reaction; and
    b) converting at least a portion of the intermediate product stream comprising one or more corresponding olefins to a product stream comprising one or more corresponding alcohols through an indirect catalytic hydration reaction.

2. The method of claim 1 wherein the catalytic oxidative dehydrogenation reaction occurs in a short contact time reactor at a gas-hourly space velocity between about 20,000 and about 200,000,000 $hr^{-1}$.

3. The method of claim 1 wherein the reactant stream comprising propane and/or one or more higher alkanes derives, at least in part, from a source of natural gas.

4. A method for the sequential hydration of two or more alcohols from two or more corresponding alkanes comprising:
    a) converting a reactant stream comprising two or more alkanes to an intermediate product stream comprising olefins; and
    b) converting one or more olefins in the intermediate product stream comprising olefins to a first product stream comprising one or more alcohols under selective hydration conditions with respect to one or more other olefins in the intermediate product stream comprising olefins through an indirect catalytic hydration reaction.

5. The method of claim 4 further comprising the additional step of converting the one or more other olefins to a second product stream comprising one or more alcohols.

6. The method of claim 4 wherein step a) comprises a catalytic oxidative dehydrogenation reaction.

7. The method of claim 6 wherein the catalytic oxidative dehydrogenation reaction occurs in a short contact time reactor at a gas-hourly space velocity between about 20,000 and about 200,000,000 $hr^{-1}$.

8. The method of claim 4 wherein the reactant stream comprising propane and/or one or more alkanes derives, at least in part, from a source of natural gas.

9. The method of claim 5 wherein the first product stream comprises isopropanol and the second product stream comprises ethanol.

10. The method of claim 5 wherein the first product stream comprises ethanol and the second product stream comprises isopropanol.

* * * * *